(12) United States Patent
Moll et al.

(10) Patent No.: US 8,736,834 B2
(45) Date of Patent: May 27, 2014

(54) MODULAR OPTICAL SENSOR SYSTEM FOR FLUID MEDIA

(75) Inventors: Georg Moll, Lauda (DE); Dominik Rabus, Fortchenberg (DE); Michael Winkler, Weissbach (DE)

(73) Assignee: Buerkert Werke GmbH, Ingelfingen (DE)

( * ) Notice: Subject to any disclaimer, the term of this patent is extended or adjusted under 35 U.S.C. 154(b) by 249 days.

(21) Appl. No.: 13/318,500

(22) PCT Filed: Apr. 27, 2010

(86) PCT No.: PCT/EP2010/002587
§ 371 (c)(1),
(2), (4) Date: Nov. 14, 2011

(87) PCT Pub. No.: WO2010/127790
PCT Pub. Date: Nov. 11, 2010

(65) Prior Publication Data
US 2012/0050730 A1 Mar. 1, 2012

(30) Foreign Application Priority Data
May 4, 2009 (DE) .................... 20 2009 006 488 U

(51) Int. Cl.
*G01N 21/05* (2006.01)
(52) U.S. Cl.
USPC .......................................... 356/246; 356/440
(58) Field of Classification Search
USPC ................................ 356/432–440, 244, 246
See application file for complete search history.

(56) References Cited

U.S. PATENT DOCUMENTS

| 4,440,497 | A  | * | 4/1984  | Carey et al. ................... 356/246 |
| 5,641,458 | A  |   | 6/1997  | Shockley, Jr. et al.                   |
| 5,734,468 | A  | * | 3/1998  | McNeal ........................ 356/319  |
| 6,369,894 | B1 |   | 4/2002  | Rasimas                                |
| 6,943,885 | B2 | * | 9/2005  | Martin ......................... 356/437 |
| 2007/0225612 | A1 | | 9/2007  | Mace                                   |
| 2011/0309841 | A1 | | 12/2011 | Oberndorfer et al.                     |

OTHER PUBLICATIONS

International Search Report dated Jul. 1, 2011.
English translation of International Report on Patentability Nov. 15, 2011.
Search Report from counterpart German Application No. 20 2009 006 488.3-52.

* cited by examiner

*Primary Examiner* — Hoa Pham
(74) *Attorney, Agent, or Firm* — Carlson, Gaskey & Olds, PC

(57) ABSTRACT

A modular optical sensor system for fluid media has a measuring module which includes an exchangeable fluid chamber and an exchangeable optic holder. The fluid chamber has an inlet and an outlet as well as a measurement space for the fluid medium. The optic holder has at least one optical transmitter and at least one optical receiver. The optic holder is inserted within the measuring module relative to the fluid chamber in such a way that the radiation emitted by the optical transmitter traverses the measurement space for the fluid medium in the fluid chamber and impinges on the optical receiver.

20 Claims, 5 Drawing Sheets

MODULAR OPTICAL SENSOR SYSTEM FOR FLUID MEDIA

RELATED APPLICATION

This is the U.S. national phase filing of International Patent Application PCT/EP2010/002587, filed 27 Apr. 2010, which claims priority to German Application No. 20 2009 006 488.3 filed May 4, 2009.

TECHNICAL FIELD

This invention relates to a modular optical sensor system for fluid media.

BACKGROUND OF THE INVENTION

Optical analysis methods for fluid media are carried out in the laboratory with special measuring apparatuses. Typical optical measurements cover the turbidity, color, or absorption of a fluid. For each optical measuring method, a separate measurement set-up is required in the laboratory. For on-site use, in particular also for monitoring optical properties of flowing media, the known measuring methods are not suitable.

SUMMARY OF THE INVENTION

A modular optical sensor system for fluid media provides great flexibility and a wide application spectrum. By means of an optic holder, which has two optical axes, a plurality of measurements can be carried out in parallel in one measurement set-up. In the transmitted-light method, for example, the absorption of a medium can be determined at two different wavelengths. The two measuring paths are arranged at an angle of 90° relative to each other.

It is, however, also possible to measure an absorption and detect the stray light parallel thereto at an angle of 90°, which is relevant for a turbidity measurement.

Due to the exchangeability of the optic holder, different kinds of optical measurements can be carried out one after the other with the same measurement set-up. The use of optical components such as light-emitting diodes (LEDs), photodiodes, laser diodes and the like leads to a very compact construction. Due to the exchangeability of the fluid chamber, the measurement can be made both in a continuous flow and with individual samples. Furthermore, closed fluid chambers can be used with a reference sample for calibration purposes. The inner surfaces of the fluid chamber can be equipped with optical elements such as lenses or gratings. Fluidic components also can be integrated into the fluid chamber, for example ventilation elements, filters, check valves, etc. Due to the exchangeability of the essential functional parts of the system, a defined starting condition always can be obtained again after an extended period of use.

The modular optical sensor system comprises an optical measuring module that includes the optic holder and an exchangeable fluid chamber. The great application flexibility here is achieved by the exchangeability of the measuring module as a whole, but also by the exchangeability of the fluidic insert.

BRIEF DESCRIPTION OF THE DRAWINGS

Further features and advantages of the invention can be taken from the following description of several embodiments with reference to the attached drawings, in which.

DETAILED DESCRIPTION

Figure 1:
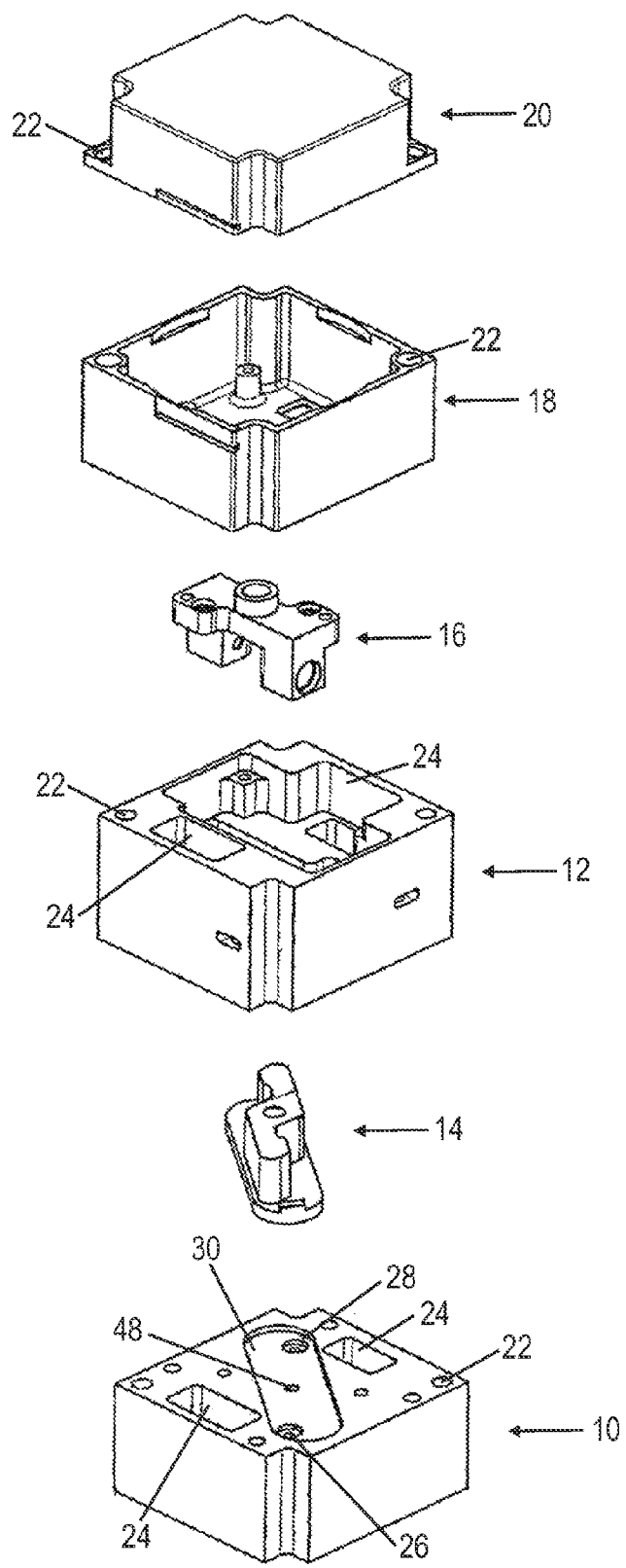
FIG. 1 shows a perspective exploded view of a modular optical sensor system in accordance with a first embodiment.

The modular optical sensor system shown in FIG. 1 includes a number of stacked cuboid modules. The entirety of the modules put together forms an appliance which is approximately cube-shaped.

A base is formed by a fluidic/electronic connection module 10. An optical measuring module 12 is put onto the same. The optical measuring module 12 accommodates an exchangeable fluid chamber 14 as well as an exchangeable optic holder 16. An electronic module 18 is put onto the measuring module 12. The electronic module 18 is closed off by a lid 20 put onto the same.

All modules are provided with through openings 22, which serve the introduction of a fastener (not shown). The connection and optical measuring modules 10, 12 furthermore are provided with recessed lead-throughs 24 which are aligned with each other and open into the electronic module 18. The connection module 10 furthermore has a fluid inlet 26 and a fluid outlet 28. Both of them open in a flat recess 30 which is formed in the surface opposite the module 12 and forms the interface for the fluid chamber 14.

Figure 2:
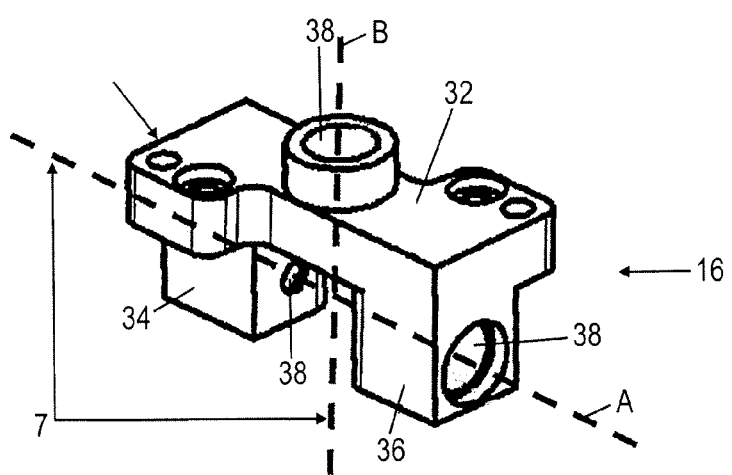
FIG. 2 shows an enlarged perspective view of an optic holder.

As shown in FIG. 2, the optic holder 16 comprises a carrier web 32 and two parallel arms 34, 36 protruding from ends of the web 32 at a distance from each other. Mounting holes 38 are provided for optical components on both the carrier web 32 and on the arms 34, 36. These optical components can be light-emitting diodes (LEDs), photodiodes, or also laser diodes. Other optical components such as mirrors, optical gratings, prisms and the like can, however, also be mounted on the optic holder 16.

Figure 3:
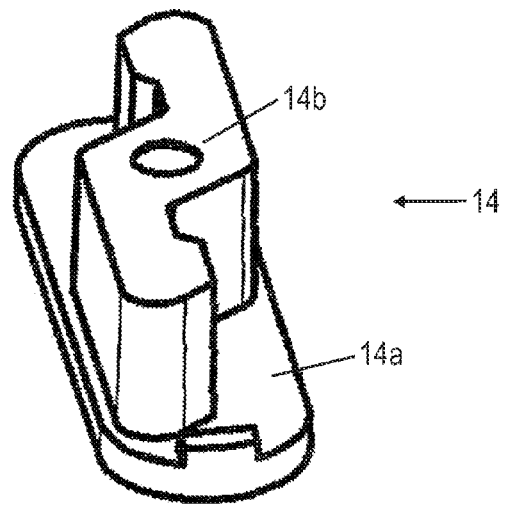
FIG. 3 shows an enlarged perspective view of a fluid chamber.
Figure 4:
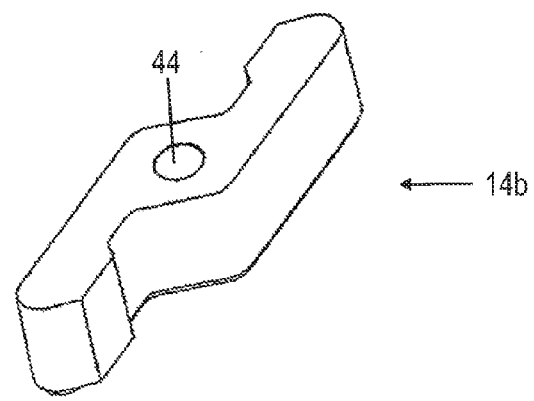
FIG. 4 shows the fluid chamber of FIG. 3 in an exploded view.
Figure 4:
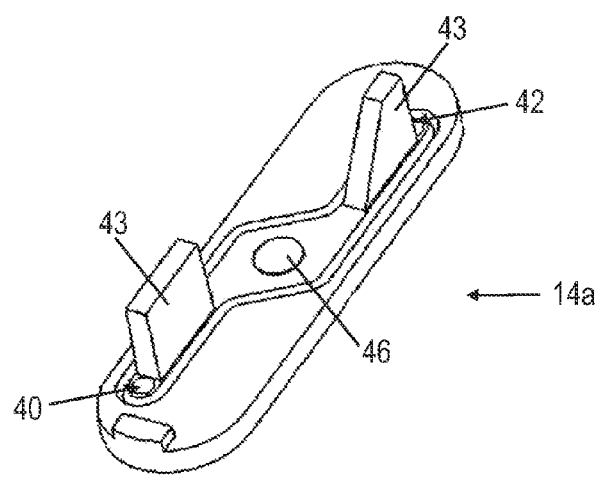

With the carrier web 32 and the arms 34, 36, the optic holder 16 encloses the fluid chamber 14 which will now be described in detail with reference to FIGS. 3 and 4.

The fluid chamber 14 includes a connecting flange 14a and a housing part 14b, which is open on one side and can be closed by the connecting flange 14a. The edge of the housing part 14b is tightly inserted into a groove of the connecting flange 14a. The connecting flange 14a can be inserted into the recess 30 (FIG. 1) of the module 10 in a tightly fitting and sealed manner and has openings 40, 42 which are aligned with the corresponding openings of the respective fluid inlet and outlet 26, 28 of the module 10. Two displacers 43 are mounted on the connecting flange 14a, and protrude into the volume of the fluid chamber.

The displacers 43 are designed to prevent an undesirable formation of air bubbles. In continuous-flow measurements, air bubbles are broken up by the displacers 43 and quickly moved on due to the flow conditions.

In its middle region, the housing part 14b forms a measurement space for the fluid medium supplied. This measurement space preferably is cube-shaped and is characterized in that the same is traversed by two measurement paths of equal length, which are vertical to each other and each extend between opposed side face centers. The optic holder 16 is put over the fluid chamber 14 in such a way that the arms 34, 36 and the carrier web 32 enclose three sides of the measurement space merging into each other. On the optic holder 16, an optical axis A is formed by two opposed optical components mounted in the mounting holes 38, which optical axis traverses the measurement space for the fluid medium in the fluid chamber 14. A second optical axis B, which is vertical to the axis A and intersects the same, is defined by a further optical component at the optic holder 16. The optical axis B traverses two opposed windows 44, 46 (FIG. 4) in the housing part 14*b* and in the connecting flange 14*a*, respectively. Opposite the window 46, an optical component 48 (FIG. 1), for example an LED, photodiode, or also a mirror, can be arranged in the recess 30 of the module 10.

The two side faces of the fluid chamber 14, which lie between the carrier arms 34 and 36 of the optic holder 16 and are adjacent to two opposed mounting holes 38, are formed similar to windows (i.e., formed in a window-like manner), so that the same are suitable for optical measurements.

As can be taken from FIG. 1, the optic holder 16 extends in a recess of the measuring module 12 approximately parallel to its walls, while the fluid chamber 14 is inserted obliquely thereto, i.e. approximately diagonally with respect to the cuboid shape of the module 12. The modules 10, 12, 18, 20 are stacked onto each other in this order and are releasably, but firmly connected, for example by using tie rods or clamping screws which are guided through the openings 22.

In use of the sensor system, the same is equipped with the types of fluid chamber 14 and optic holder 16 as required for the respective application. Before commencement of the actual measurements, it may be expedient to perform a calibration of the system by temporarily inserting a fluid chamber in which a reference sample is firmly enclosed. The measurements can then be made continuously or sample by sample, in that the fluid to be measured is supplied to the fluid chamber 14 via the fluid inlet 26, which fluid then exits via the fluid outlet 28. Depending on the type of optical components used, with which the optic holder 16 is equipped, measurements of the turbidity, color, absorption etc. can then be made in transmitted light. It is also possible to carry out a measurement in transmitted light and a stray-light measurement parallel thereto at an angle of 90° by using a single measurement set-up. The measurement signals are processed with an electronic evaluation unit, which is accommodated in the electronic module 18.

Figure 5:
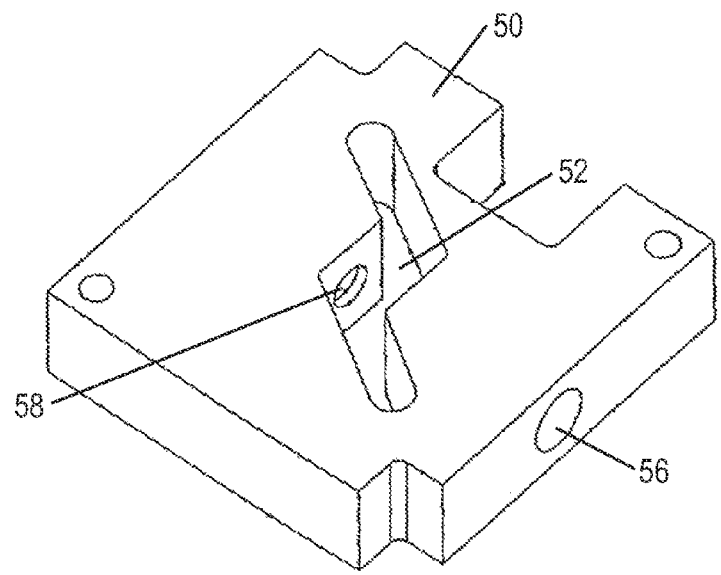
FIG. 5 shows a perspective view of an optical measuring module for use in a modular sensor system.
Figure 6:
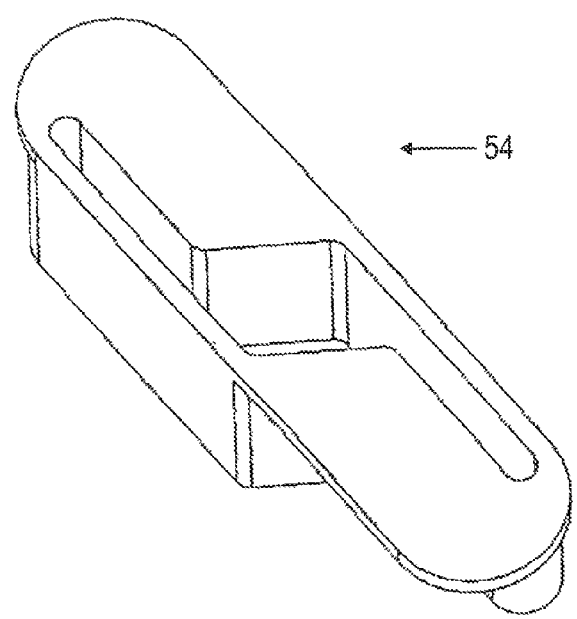
FIG. 6 shows a perspective view of an insert for the measuring module of FIG. 5.

The design of an optical measuring module as shown in FIGS. 5 and 6 can be used instead of the measuring module 12 with fluid chamber 14 and optic holder 16. FIG. 5 shows a cuboid carrier body 50 which can be assembled with further cuboid or plate-shaped modules in a similar way as shown in FIG. 1. The carrier body 50 includes a generally diagonally oriented recess 52, into which the insert 54 shown in FIG. 6 can accurately be inserted. The insert 54 forms a fluid chamber, similar to the fluid chamber 14 of the embodiment described above. The cuboid carrier body 50 is provided with opposed mounting holes 56, 58 for optical components. The optical axis defined by these mounting holes traverses the middle part of the insert 54 and thus the fluid medium enclosed or flowing therein, like in the embodiment described above.

Figure 7:
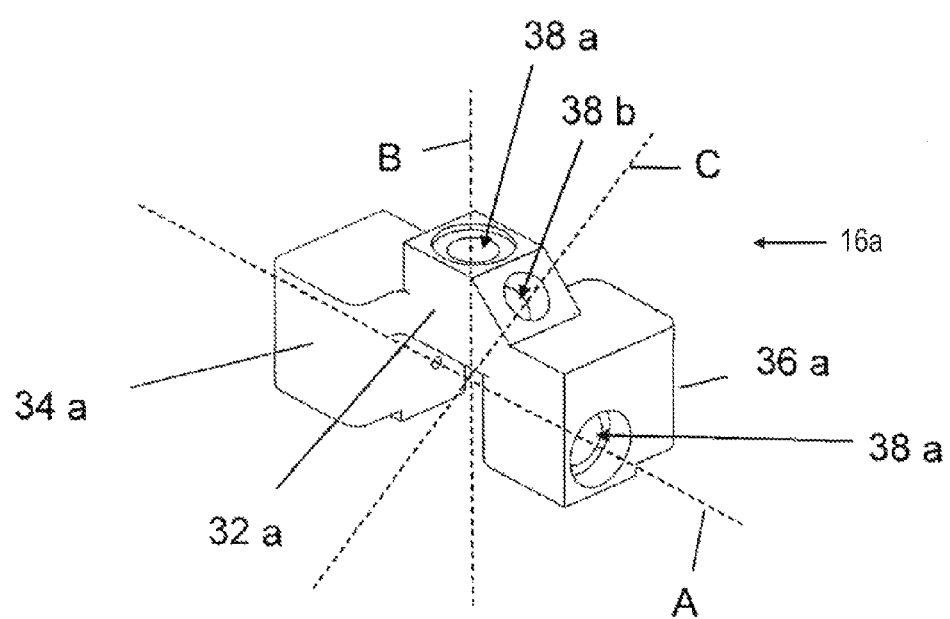
FIG. 7 shows a development of the optic holder shown in FIG. 2.

The embodiment of the optic holder 16*a* as shown in FIG. 7 comprises a middle carrier web 32*a* and two parallel arms 34*a*, 36*a* protruding from ends of the web 32 at a distance from each other. Mounting holes 38*a* are provided for optical components on both the carrier web 32*a* and on the arms 34*a*, 36*a* mounting holes 38*a* are provided for optical components. These optical components can be light-emitting diodes (LEDs), photodiodes, phototransistors, or also laser diodes. Other optical components such as mirrors, optical gratings, prisms and the like can, however, also be mounted on the optic holder 16*a*. The mounting holes 38*a* for the optical components initially are arranged as shown in FIG. 2, such that two optical axes A and B are defined, which can intersect each other. In addition a further mounting hole 38*b* is provided on the carrier web 32*a*, which provides for a third optical axis C which is inclined against the axes A and B under an angle of 45° and can intersect both axes. If a light source is inserted into this mounting hole 38*b*, stray light can be measured with a light receiver which is inserted into a mounting hole of the carrier web 32*a*, which stray light is emitted by an opaque or dispersive medium contained in the fluid chamber 14 (FIG. 3). For detecting reflected light, a further mounting hole for a light receiver can be arranged symmetrical to the mounting hole 38*b* on the carrier web 32*a*.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A modular optical sensor system for fluid media, comprising:
    a measuring module which includes an exchangeable fluid chamber and an exchangeable optic holder, wherein:
    the exchangeable fluid chamber includes an inlet and an outlet as well as a measurement space for a fluid medium;
    the exchangeable optic holder includes at least one optical transmitter and at least one optical receiver;
    the exchangeable optic holder is insertable within the measuring module relative to the exchangeable fluid chamber such that radiation emitted by the optical transmitter traverses the measurement space for the fluid medium in the exchangeable fluid chamber and impinges on the optical receiver; and
    a fluidic/electronic connection module wherein an optical component is arranged in the fluidic/electronic connection module.

2. The sensor system according to claim 1, wherein the measuring module is assembled to a cube-shaped sensor device with an electronic module and the fluidic/electronic connection module.

3. The sensor system according to claim 1, wherein the exchangeable optic holder includes mounting holes for optical components.

4. The sensor system according to claim 1, wherein the exchangeable optic holder carries optical components which are arranged along at least two different optical axes.

5. The sensor system according to claim 1, wherein the exchangeable optic holder includes two spaced parallel arms which carry one optical component each and enclose the exchangeable fluid chamber.

6. The sensor system according to claim 5, wherein the exchangeable optic holder carries one optical component each on three sides merging into each other, which all are adjacent to sides of the exchangeable fluid chamber.

7. The sensor system according to claim 5, wherein the measurement space of the exchangeable fluid chamber is arranged between the spaced parallel arms of the exchangeable optic holder.

8. The sensor system according to claim 5, wherein the exchangeable optic holder carries at least one optical component each on three sides merging into each other, which all are adjacent to sides of the exchangeable fluid chamber, and in addition on a surface inclined at an angle to the exchangeable fluid chamber.

9. The sensor system according to claim 1, wherein the exchangeable fluid chamber is composed of a connecting flange and a housing part with an open side which is closed by the connecting flange.

10. The sensor system according to claim 9, wherein the connecting flange includes displacers which protrude into a volume of the exchangeable fluid chamber.

11. The sensor system according to claim 9, wherein the connecting flange is insertable into a recess of the fluidic/electronic connection module in a sealing and positive manner.

12. The sensor system according to claim 1, wherein the exchangeable fluid chamber is obliquely orientated relative to the exchangeable optic holder.

13. The sensor system according to claim 1, wherein the fluidic/electronic connection module includes a recess to seat the exchangeable fluid chamber.

14. The sensor system according to claim 13, wherein the recess includes a fluid inlet and a fluid outlet, and wherein the inlet of the exchangeable fluid chamber is in fluid communication with the fluid inlet and the outlet of the exchangeable fluid chamber is in fluid communication with the fluid outlet.

15. The sensor system according to claim 14, wherein the measuring module includes a first mount interface and a second mount interface opposite of the first mount interface, and wherein the measuring module is configured for attachment to the fluidic/electronic connection module via the first mount interface, and including an electronic module that is configured for attachment to the measuring module via the second mount interface.

16. The sensor system according to claim 15, wherein the measuring module and fluidic/electronic connection module each include at least one recess lead-through that is open to the electronic module.

17. The sensor system according to claim 16, wherein the fluidic/electronic connection module, the measuring module and electronic module are attached to each other with at least one common fastener.

18. The sensor system according to claim 13, wherein the exchangeable fluid chamber includes a connecting flange that fits within the recess and a housing part that is seated on the connecting flange to at least partially enclose the measurement space.

19. The sensor system according to claim 18, wherein the connecting flange includes displacers which protrude into a volume of the exchangeable fluid chamber.

20. An optical measuring module for use in a modular sensor system comprising:
a plurality of stacked modules including a plate-shaped or cuboid carrier body which includes a recess for accurately accommodating an exchangeable insert and mounting holes for receiving optical components, and wherein the exchangeable insert forms a fluid chamber which includes a fluid inlet, a fluid outlet, and a measurement space which is traversed by an optical axis formed between the optical components, and including a fluidic/electronic connection module that seats the exchangeable insert, and wherein an optical component is arranged in the fluidic/electronic connection module.

* * * * *